[19] United States Patent
Helting

[11] 4,200,627
[45] * Apr. 29, 1980

[54] ATOXIC, IMMUNOGENIC PRODUCT OF TETANUS TOXIN

[75] Inventor: Torsten B. Helting, Marburg an der Lahn, Fed. Rep. of Germany

[73] Assignee: Behringwerke Aktiengesellschaft, Marburg an der Lahn, Fed. Rep. of Germany

[*] Notice: The portion of the term of this patent subsequent to Feb. 8, 1994, has been disclaimed.

[21] Appl. No.: 971,848

[22] Filed: Dec. 21, 1978

Related U.S. Application Data

[63] Continuation of Ser. No. 819,939, Jul. 28, 1977.

[30] Foreign Application Priority Data

Jul. 31, 1976 [DE] Fed. Rep. of Germany ....... 2634584

[51] Int. Cl.$^2$ .............................................. A61K 39/08
[52] U.S. Cl. ...................................................... 424/92
[58] Field of Search ........................................... 424/92

[56] References Cited

FOREIGN PATENT DOCUMENTS 2355094 11/1973 Fed. Rep. of Germany.
2457047 12/1974 Fed. Rep. of Germany.
2634584 7/1976 Fed. Rep. of Germany.

OTHER PUBLICATIONS

Helting, T. B., Zwisler, O. J. Biol. Chem. 252(1):187-193, 10 Jan. 1977, Structure of Tetanus Toxin I. Breakdown of the Toxin Molecule and Discrimination Between Polypeptide Fragments.
Helting, T. B., Zwisler, O. Wiegant, H. 252(1):194-198, 10 Jan. 1977, Structure of Tetanus Toxin II. Toxin Binding to Ganglioside.
Helting, T. B., Ronneberger, H. J., Vollerthun, R., Neubauer, V. J., Biol. Chem. 253(1):125-129, 10 Jan. 1978, Toxicity of Papain—Digested Tetanus Toxin. Pathological Effect of Fragment B in the Absence of Spastic Paralysis.
Helting T., Zwisler, O., Biochem. Biophysres Commun. 57(4) 1974: 1263-1270, Enzymatic Breakdown of Tetanus Toxin.
Helting, T., Zwisler, O., Abstr. Annu. Meet Am Soc. Microbiol. 77 1977 16 Analysis of the Protective Immune Response to Papain Digestion Products of Tetanus Toxin.

Primary Examiner—Shep K. Rose
Attorney, Agent, or Firm—Curtis, Morris & Safford

[57] ABSTRACT

What is disclosed is a method for obtaining an atoxic, immunogenic product from tetanus toxin by treating tetanus toxin with a proteinase. The product, which is different from known fragment C of tetanus toxin, can be used for making a vaccine.

4 Claims, No Drawings

ATOXIC, IMMUNOGENIC PRODUCT OF TETANUS TOXIN

This is a continuation of application Ser. No. 819,939, filed July 28, 1977.

The present invention relates to an atoxic, immunogenic product of tetanus toxin.

The invention provides an atoxic, immunogenic product which may be obtained from tetanus toxin by means of a proteinase. It also provides a tetanus vaccine containing the novel product.

As has already been known, tetanus toxin is highly toxic towards mammals and also humans and must be detoxicated, in order to be used as an immunizing agent. It has been known to detoxicate tetanus toxin by treating it with formaldehyde. It has also been known that an atoxic, immunogenic product can be obtained by a treatment of tetanus toxin with a proteinase. This atoxic, immunogenic product is called fragment C of the tetanus toxin in the scientific literature.

It was a surprising fact which could not have been foreseen that in the treatment of tetanus toxin with a proteinase, preferably with papain, a further substance having especially advantageous properties is formed which can be characterized chemically in a definite manner and which may be isolated according to known biochemical processes.

The particularly advantageous properties of the product, termed fragment B, include the absence of toxicity and the perservation of the immunogenicity of the same. These properties make the product suitable as a component of vaccines against tetanus.

The present invention therefore provides an atoxic, immunogenic product which may be obtained from tetanus toxin by treating the same with a proteinase, preferably with papain, which product is characterized by the following parameters:

1. Sedimentation constant $S°_{20w} 5.66 \pm 0.34$
2. Immunologic reaction with tetanus antitoxin: partially identical with that of tetanus toxin.
3. Immunologic reaction with fragment C: not identical.
4. Molecular weight, determined by gel electrophoresis in sodium dodecylsulfate, of $95,000 \pm 5,000$.
5. Cleavable by reduction into a sub-unit having a molecular weight of $45,000 \pm 2,500$ and a sub-unit immunologically identical with the known derivative of the light chain of tetanus toxin, having a molecular weight of $48,000 \pm 2,500$ (each time determined by sodium dodecyl-sulfate electrophoresis).

The variations shown in the parameters are due to the limits of error within the methods of determination.

The sedimentation constant was determined in an aqueous solution of 0.2 molar NaCl, 0.02 molar $Na_2HPO_4$, 0.03 molar $NaH_2PO_4$ at a pH of 6.8 according to T. Svedberg and K. O. Pedersen, "Ultra-centrifuge", The Clarendon Press, Oxford, 1940, in an overlayer cell of an analytical ultracentrifuge, with reference to Vinograd, Proc.Acad.Sci. USA 49, 902 (1963). The overlayering action of the test solution containing the product of the invention was effected on a 1 molar NaCl solution having a pH value of 7.0.

The immunologic reactivity was examined using antisera which were obtained by the immunisation of rabbits with tetanus toxoid or with fragment B of the invention. Use was made of the known diffusion technique. By means of this technique it can be shown that the formerly described fragment C is clearly distinguished from fragment B of the invention. As could further be shown, fragment B can be dissociated into two fragments, one of which shows the same immunologic behavior as the derivative of the light chain described in U.S. Pat. No. 4,029,765 granted June 14, 1977.

Gel electrophoresis in a 7% polyacrylamide gel with the use of sodium dodecylsulfate as a component of the electrophoresis buffer has been carried out according to K. Weber and M. Osborn, J.Biol.Chem., 244, 4406–4412 (1969). Prior to carrying out the gel electrophoresis, the samples to be analyzed were mixed in an aqueous solution with sodium dodecylsulfate up to a concentration of 1% and were kept for 1 minute in boiling water. The calculation of the molecular weight is effected by a comparison with standard substances for determining the moleculr weight (Aldolase and Katalase which may be obtained by Messrs. Boehringer, Mannheim, No. of Cat. 15,575—"Eichproteine Grösse II"). The calculation method has been indicated in the above-cited paper by Weber and Osborn.

The novel atoxic, immunogenic product labelled fragment B of the tetanus toxin may be obtained, by treating tetanus toxin with a proteinase. More in particular (as also described in U.S. Pat. No. 4,007,265 granted Feb. 1, 1977), tetanus toxin is treated with a peptidepeptidohydrolase such as papain, trypsin, and the bacterial proteinases from *B. subtilis*, in a medium which does not lead to an irreversible denaturation of the protein body of tetanus toxin, i.e. at a pH between 5 and 10. According to a preferred embodiment, fragment B is obtained by the treatment of tetanus toxin, which may be produced from culture filtrates of Clostrium Tetani by way of ion exchange chromatography, with papain, preferably in the form of a substance bound to a carrier, in the presence of a reducing agent.

In this process it has proved to be advantageous to choose an incubation temperature which is higher than usual, i.e. between 30° and 60° C., preferably between 45° and 55° C. By this measure it is possible to increase the yield of the product of the invention. Following the proteolytic action on the tetanus toxin, the enzyme bound to a carrier is eliminated from the reaction mixture, suitably by way of centrifuging, and the remaining solution is subjected to a fractionation through a molecular sieve. In this process the use of dextran cross-linked with epichlorhydrin has proved to be advantageous, for example Sephadex ® G 100 of Firm Pharmacia, Uppsala or Ultrogel ® of LKB, Bromma or bio-gel p ® of Bio-Rad Laboratories, Richmond, Calif.

In case a soluble enzyme preparation is used, the enzyme is separated during fractionation through the molecular sieve.

Once fragment B has been obtained in this manner, an antiserum may be prepared with the same by the immunization of test animals with fragment B, and by means of said antiserum it is then possible to obtain an immuno-adsorbing agent in the usual manner. This agent serves in its turn to extract fragment B in a particularly pure form from the incubation mixture of said fermentation solution.

It is also possible to eliminate fragment C or tetanus toxin from a mixture with fragment B by immuno-adsorptive measures. For this purpose, an antiserum against the known fragment C is at first prepared. By means of this antiserum, an immuno-adsorbing agent can be obtained in known manner. Said agent is suitable in its turn to eliminate the remainder of fragment C and of tetanus toxin from fragment B, since fragment C as well as tetanus toxin react with the anti-fragment C-serum, however, fragment B does not. Other processes of isolation, known to those skilled in the art for separating proteins having a different electric charge, are also successful. They include above all electrophoretic processes as well as processes of ion exchange chromatography.

The pure fragment B from tetanus toxin which may be obtained in this manner proves to be non-toxic as compared with tetanus toxin. Whereas $30 \times 10^6$ min.lethal doses are detected per mg of tetanus toxin, fragment B has 5 min.lethal doses per mg. With regard to the toxic symptoms, fragment B is seen to be completely different from tetanus toxin; it does not show the symptoms characterized by spastic paralysis. In spite of the reduction of the toxicity to $1:6 \times 10^6$ it is advantageous to treat fragment B with an aldehyde, as has been described in the following.

For this process the product obtained by means of proteinases is treated after its isolation at a protein concentration of about 1 mg of protein per ml or less in a buffer solution having a pH value of from 6.0 to 8.5, preferably 7.8, and a molarity in the range of from 0.01 to 0.2 moles per liter with 0.015 to 0.3 moles per liter of an aliphatic mono- or dialdehyde of 1 to 6 carbon atoms, preferably formaldehyde, during 14 to 28 days at a temperature in the range of from 20° to 37° C. If desired, the product may be subjected to a dialysis of 10 to 20 hours, preferably 15 hours, against a physiologically acceptable solution, such as 0.15 molar sodium chloride, and/or it may be filtered under sterile conditions. For preparing the vaccine, the product is suitably also mixed with an adjuvant, for example, aluminum hydroxide. By dilution with a physiologically acceptable solution, such as 0.15 molar sodium chloride solution, the concentration is adjusted to the desired antigen content.

These vaccines may be used by themselves, but also in combination with other vaccines. For combination there are suitable, above all, diphtheria toxoid, pertussis immunogenic agents, poliomyelitis viruses, or measles viruses. By way of adsorption tests it can be shown that about one half of all protecting antibodies directed against tetanus toxin are directed against fragment B.

The following Examples serve to further illustrate the present invention.

EXAMPLE 1

Clostrium-tetani are fermented in a Latham medium. The toxin formed in this process is adsorbed on diethylaminoethyl cellulose ion exchangers and is eluted by a phosphate buffer having a pH value of 7 from 0.01 mole to 0.4 mole. The fractions containing the toxin are again separated by chromatography in a column which is filled with Sephadex ® G 100, and the fractions containing the toxin are extracted and combined.

2.5 Grams of tetanus toxin in a solution having a final concentration of 15 mg of tetanus toxin/ml in a 0.01 molar phosphate buffer of a pH of 6.5 containing 0.01 mole of $Na_2EDTA$ and 0.001 mole of cystein-HCl are mixed with 40 mg of papain. The papain contains 30 units of enzymatic activity/mg of substance. At first, the mixture is maintained for 1 hour at 45° C., and thereafter for another 2 hours at 55° C.

For the separation of the tetanus toxin there may be used preferably also papain bound to a carrier.

For this purpose, a solution of 50 mg/ml of papain, dialyzed against 0.1 molar $Na_2CO_3$ buffer of a pH 10.0, is combined with an agarose gel activated with cyanobromide and the mixture is maintained for 24 hours at 4° C. The reaction product, washed several times with a solution containing 4 moles of urea and 0.5 mole of NaCl per liter, is used in a manner analogous to that of the soluble enzyme for the proteolytic separation of the tetanus toxin.

Upon cooling of the mixture, the volume is concentrated by means of an ultrafilter, and the mixture is then introduced into a column of a length of $10 \times 100$ cm filled with Sephadex ® G 100. The elution is effected with a 0.1 molar trishydroxymethylaminomethane-hydrochloric acid buffer having a pH value of 8.0 and containing 1 mole of NaCl.

During the elution, the adsorption at a wave length of 280 nm is measured continuously. The fractions showing an adsorption in this range are collected separately. There are formed 4 fractions, the first of which represents a double peak.

In the course of repeated chromatography carried out under the same conditions, the two peaks are separated, and finally the second peak is isolated. This latter peak contains the atoxic, immunogenic product of the invention, the fragment B from tetanus toxin.

The fragment B of the invention can be obtained in a particularly simple manner if an antiserum directed against the known fragment C (10 ml with 1,000 IU/ml) is bound in the usual manner to agarose activated by BrCN, and a preparation of fragment B which has been partially purified by gel chromatography is subsequently mixed with such an immuno-adsorbing agent. After 60 minutes of stirring, the gel is separated together with the impurities bound to it, and fragment B is obtained by another gel chromatography.

It is also possible to neutralize the impurities by adding anti-fragment C-antiserum (IgG fraction) and to separate the immune complex compounds from fragment B by way of gel chromatography.

Finally, fragment B of the invention may also be obtained if an immuno-absorbing agent for fragment B is prepared via an antiserum, with the aid of a fragment B once prepared. For this purpose, known processes may be applied. By means of the immuno-adsorbing agent, fragment B is absorbed selectively from the mixture with other reaction products from the proteinase treatment of tetanus toxin, whereupon it may be eluted selectively from the immuno-absorbing agent.

EXAMPLE 2

Fragment B is diluted with 0.1 molar phosphate buffer solution of a pH of 6.5 to 200 μg of protein per ml, mixed with 0.06% formaldehyde and allowed to stand at 37° C. for 21 days. Thereafter, the solution is dialyzed for 16 hours against several times its volume of 0.15 molar sodium chloride solution and is then processed in the usual manner into a vaccine.

What is claimed is:

1. An atoxic immunogenic product from tetanus toxin prepared by cleaving tetanus toxin by treating it with a peptide-peptidohydrolase at a pH between 5 and 10 so not to cause the irreversible denaturization of the protein body of tetanus toxin and then isolating from the reaction mixture said product, having
   (a) a sedimentation constant of $S°_{20}w 5.66 \pm 0.34$,
   (b) an immunologic reaction with tetanus antitoxin partially identical with that of tetanus toxin, (c) an immunologic reaction not identical with that of fragment C of tetanus toxin,
(d) a molecular weight of 95,000±5,000 as determined by gel electrophoresis in sodium dodecylsulfate, and
(e) an ability to be cleaved into a sub-unit having a molecular weight of 45,000±2,500 and a sub-unit having a molecular weight of 48,000±2,500, as determined by gel electrophoresis in sodium dodecylsulfate, said latter sub-unit being immunologically identical with the known derivative of the light chain of tetanus toxin.

2. An atoxic immunogenic product prepared as in claim 1 but wherein the product of claim 1 is additionally treated with from 0.015 mole/liter to 0.3 mole/liter of an aliphatic mono-aldehyde or aliphatic dialdehyde having up to 6 carbon atoms for 14 to 28 days at a pH from 6.0 to 8.5 and at a temperature from 20° C. to 37° C.

3. A tetanus vaccine comprising the atoxic immunogenic product of claim 1 together with an adjuvant.

4. A tetanus vaccine comprising the atoxic immunogenic product of claim 2 together with an adjuvant.

* * * * *